United States Patent
Engel

(10) Patent No.: US 10,551,369 B2
(45) Date of Patent: Feb. 4, 2020

(54) PROBABILISTIC DEFECT DETECTION IN LAID FIBER RIBBONS

(71) Applicant: AIRBUS DEFENCE AND SPACE GMBH, Ottobrunn (DE)

(72) Inventor: Franz Engel, Ottobrunn (DE)

(73) Assignee: Airbus Defence and Space GmbH, Taufkirchen (DE)

( * ) Notice: Subject to any disclaimer, the term of this patent is extended or adjusted under 35 U.S.C. 154(b) by 435 days.

(21) Appl. No.: 15/224,022

(22) Filed: Jul. 29, 2016

(65) Prior Publication Data

US 2017/0030886 A1     Feb. 2, 2017

(30) Foreign Application Priority Data

Jul. 31, 2015   (DE) .......................... 10 2015 009 728

(51) Int. Cl.
*G01N 33/36* (2006.01)
(52) U.S. Cl.
CPC .................................... *G01N 33/36* (2013.01)
(58) Field of Classification Search
CPC ...................................................... G01N 33/36
USPC ........................................................... 702/63
See application file for complete search history.

(56) References Cited

U.S. PATENT DOCUMENTS

| | | | |
|---|---|---|---|
| 6,272,437 B1* | 8/2001 | Woods ................... | G01N 23/04 700/110 |
| 2006/0181700 A1* | 8/2006 | Andrews ................ | G01N 21/21 356/237.2 |
| 2006/0287836 A1 | 12/2006 | Mateo | |
| 2008/0075353 A1* | 3/2008 | Tek ...................... | G01N 21/4738 382/145 |
| 2011/0218741 A1* | 9/2011 | Hirano ............... | G01N 27/9006 702/38 |
| 2014/0267693 A1* | 9/2014 | Newman ............... | G06T 7/0004 348/128 |
| 2015/0046098 A1 | 2/2015 | Jack et al. | |

FOREIGN PATENT DOCUMENTS

EP           2 653 829 A1       10/2013

OTHER PUBLICATIONS

German Office Action for DE 10 2015 009 728.8 dated Mar. 18, 2016.
R. Schmitt et al., Laser light-section sensor automating the production of textile-reinforced composites. Proc. SPIE vol. 7356, Optical Sensors 2009, 73560P.
European Search Report for European Application No. 16181127.8 dated Dec. 5, 2016.

* cited by examiner

*Primary Examiner* — Ricky Ngon
(74) *Attorney, Agent, or Firm* — Jenkins, Wilson, Taylor & Hunt, P.A.

(57) ABSTRACT

A method for a probabilistic detection of defects in ribbons of material laid on a fiber composite workpiece. The method includes detecting at least one surface profile of a workpiece having laid material ribbons and locating a surface profile entry in a database. In this case, the surface profile entry provides an assignment of the surface profile to a defect type and to a hit probability that the detected surface profile is based on a defect of the defect type.

11 Claims, 3 Drawing Sheets

PROBABILISTIC DEFECT DETECTION IN LAID FIBER RIBBONS

CROSS-REFERENCE TO RELATED APPLICATION

This application claims priority to DE 10 2015 009 728.8 filed Jul. 31, 2015, the entire disclosure of which is incorporated by reference herein.

TECHNICAL FIELD

The present disclosure relates to a method for the probabilistic detection of defects in ribbons of material, which have been laid on a fiber composite workpiece, by a database. The disclosure herein also relates to a method for creating a correspondingly suitable database. Finally, the disclosure herein relates to a computer-readable storage medium having instructions for implementing a method for the probabilistic detection of defects, to an inspection device for checking a fiber composite material and to an installation for the automated production of fiber composite components.

BACKGROUND

Fiber composite plastics are used in many areas. In particular, carbon fiber-reinforced plastics are used, for example in industrial components, in aerospace technology and in sports equipment. The production of this type of fiber composite plastics can comprise in particular automatic layer depositing processes. Using a laying head, dry or pre-impregnated fibers (for example carbon fibers) are laid in narrow ribbons next to one another and also in a plurality of superimposed layers in a forming tool.

In this process, various defects can arise. For example, if a layer is deposited incorrectly, undesirable twists, overlaps, gaps or material folds can occur. In addition, foreign material can arrive in or on the layers; this type of undesirable material can originate from the installation itself (for example abraded material in the laying head) or, in the case of an open tool, can enter from the surroundings as dirt.

To avoid disadvantageous consequences, layers which are deposited according to the prior art are examined visually by staff for such defects after each completed layer. For this purpose, the relevant inspectors can walk on the forming tool, and sometimes there are also lifting systems by which the workers can be suspended above the mould to inspect the laid material.

When a defect has been established, in order to decide on the course of action to be taken, it is furthermore advantageous to type the defect whereby the nature of the defect is determined, i.e. for example it is established that a twist, a material gap or the like is present. According to the prior art, this typing is also effected by a visual check carried out by staff who carry out a corresponding assignment of a detected defect.

The mentioned checking and typing mechanisms are complex, demand a great amount of time and are often inaccurate. Furthermore, large control surfaces in particular often require a systematic guided observation which is often difficult to maintain, so that defects can easily be overlooked. Finally, the staff who are walking on the tool or are guided above the material, or also the corresponding lifting systems can themselves damage or soil the deposited layers.

SUMMARY

One of the ideas of the present disclosure is to provide a method, by which defects in ribbons of material which have been laid on a fiber composite workpiece can be detected while avoiding the aforementioned disadvantages.

A first method according to the disclosure herein is used for a probabilistic detection of defects in ribbons of material laid on a fiber composite workpiece; in this case, the material of the material ribbons can comprise in particular uncured carbon fiber-reinforced plastics. A method of this type comprises detecting at least one surface profile of a workpiece having laid material ribbons. In this case, the surface profile can relate to only one locally limited region of the surface of the workpiece, in particular to a portion of a line; particularly preferred are embodiments in which the surface profile relates to a linear portion which intersects at least one laid material ribbon. The mentioned first method according to the disclosure herein also comprises locating a surface profile entry in a database; the surface profile entry provides (i.e. allows, for example comprises) an assignment of the detected surface profile to a defect type and to (a value) of a probability that the detected surface profile is actually based on a defect of the (thus assigned) defect type; to distinguish this probability (or this probability value) from other probabilities considered here, this probability is designated herein as a "hit probability" (because it indicates a probability that the assignment of the surface profile to the defect type is consistent with reality).

The term "probability" according to general linguistic usage is occasionally identified here by a value respectively assigned thereto. The fundamental assignment can be made, for example, on the basis of known data (for example empirical values), on the basis of at least one statistical method and/or on the basis of machine learning.

The hit probability is preferably positive (i.e. greater than 0); in particular the database does not need to include any assignments having a probabilistic impossibility and therefore the size of the database can be kept relatively small and an entry which has been found is particularly useful.

A method according to the disclosure herein thus allows an automated detection of defects which can be exhibited by the laid ribbons of material; the detection comprises a probabilistic typing of a respective defect. Thus, complex inspections, which are susceptible to errors, of a workpiece by staff can be at least reduced and in the case of a corresponding defect, appropriate measures can nevertheless be taken for the respective type of defect, which measures can, if appropriate, be specifically adapted to the type of defect.

According to some embodiments, the detection of the surface profile in a first method of this type according to the disclosure herein comprises scanning at least one surface portion of the workpiece by at least one sensor device. The sensor device can comprise, for example a laser light section sensor (or triangulation sensor). Scanning can, but does not have to be carried out in a planar manner. In particular, scanning can be carried out along a line or curve which may intersect at least one material ribbon, for example a plurality of material ribbons. In this way, in particular defects at the transitions of the material ribbons, for example gaps or overlaps can be detected.

According to an advantageous variant, a first method according to the disclosure herein comprises a characterization of the at least one (or every) detected surface profile by a (respective) sequence which comprises information about step directions, step widths and/or step heights which occur in the surface profile (and which may allow for conclusions to be drawn about an associated step arrangement (for example sequence). The sequence is thereby preferably a digital representation of the real surface profile. The step directions can be characterized, for example in binary manner as "rising" or "falling" (relative to the respective background), or angular regions can be indicated into which a portion of the surface profile falls. The characterization may take place automatically; in particular it can comprise an automatic generation of the sequence.

The sequence makes it possible for a smaller representative from the volume of data having a predetermined structure to be used in the further course of the method for the surface profile. In particular, locating the surface profile entry can be simplified and accelerated in that it is carried out on the basis of the sequence.

According to some embodiments, the characterization comprises a categorization of step widths into a predetermined number of width categories and/or a categorization of information about occurring step heights which is optionally contained in the sequence. The width categories comprise widths which are located within an interval which can be predetermined by a predetermined minimum step width and by a predetermined maximum step width; the individual categories are preferably thus substantially based in each case on intervals of the same size. Information about occurring step heights which is optionally contained in the sequence can be categorized, for example by the particular number of superimposed layers of ribbons which form the relevant step.

A volume of data of a digital representative of the surface profile can be further reduced in this way and in particular the locating procedure can be further accelerated.

In some embodiments, the locating procedure takes place by an automated, successive comparison (for example corresponding to a step arrangement) of individual step directions and/or step widths and/or step heights, described by the sequence, using nodes of a search tree, by which the database preferably is or can be structured. It may be particularly advantageous if the search tree comprises a neural network.

The locating procedure can thus be achieved by systematic comparisons of a particularly small number, which accelerates the method particularly if the database comprises a large number of entries.

As mentioned, the hit probability in the assignment can be based on known data (for example empirical values), on machine learning steps and/or on at least one statistical method. An embodiment is particularly preferred in which the hit probability includes (or comprises) a probability that the surface profile is actually detected when a defect of the defect type occurs; thus in this embodiment, the last mentioned probability (which herein is called the "surface profile probability") is considered for the hit probability in the assignment of a value. Alternatively or in addition, preferably the hit probability can analogously include (comprise) a probability that the detected surface profile contains at least one measured defect (i.e. that the detection thereof is based on a measured defect) and/or that a defect of the defect type (assigned to the surface profile) actually occurs on the fiber composite workpiece; the last two mentioned probabilities are referred to herein as "measured defect probability" or "occurrence probability" to provide a clearer distinction.

These embodiments allow particularly reliable, realistic hit probabilities in the assignments and thereby a particularly reliable probabilistic detection of defects including the typing thereof.

The defect type provided by the assignment and/or the associated hit probability are preferably determined automatically; the respective values can be, for example output, stored and/or used for at least one automatic calculation.

According to some variants, a first method according to the disclosure herein comprises the output of at least one defect type assigned to the surface profile entry as well as the output of the associated hit probability on an output device. In this case, in connection with the defect type and the hit probability, information is preferably also output which indicates the position of the workpiece in which the surface profile was detected.

A user can thereby follow the inspection progress and can recognise in particular when a defect in the laid material ribbons has been detected and when an associated counterpart has been located in the database. Furthermore, the user learns the assigned hit probability and optionally also receives an indication of the position of the suspected defect. This information makes it easy for the user to draw conclusions about suitable measures which have to be taken.

In some embodiments in which the mentioned output comprises a determination that the hit probability reaches or exceeds a predetermined minimum value, the minimum value may be adjusted by a user.

This allows an output of only those defect types assigned to the surface profile which are relevant to practice or (when there is an adjustability of the minimum value) relevant to the respective case. In particular, an output can be suspended if the hit probability (for the assigned defect type) which is assigned to the surface profile and is provided by the located surface profile entry falls below the minimum value.

The database can also comprise, in addition to the located entries, one or more further entries having one or more assignment(s) of the surface profile to the same or to other defect type(s) and associated defect type probability/probabilities:

In particular, the located surface profile entry can be a first surface profile entry, the assigned defect type can be a first defect type and the assigned hit probability can be a first hit probability. The method can also comprise a locating of at least one further surface profile entry in the database which provides a (further) assignment (i.e. which contains information which allows the assignment), specifically an assignment of the surface profile to at least one further defect type which differs from the first defect type and to at least one further hit probability (as a probability that the detected surface profile is based on a defect of the at least one further defect type).

It is thus considered that different defect types can lead to the same surface profile: on the one hand, the defects of a different defect type can have surface profiles which match in portions (for example along particular lines), on the other hand, measured defects can lead to matching surface profiles, in spite of different underlying defect types. The mentioned variant thus provides comprehensive information about different possible defect types on which the detected surface profile could theoretically be based, and also provides the associated hit probabilities. The at least two defect types, assigned thus, with associated hit probabilities are preferably output at an output device as described above (for example if the hit probabilities reach or exceed a minimum value).

Thus, the user receives an informed overview of defects of particular defect types which may be present on the workpiece, and the user can estimate the quality of the workpiece thereby and by the associated hit probabilities, and if necessary can take suitable measures.

The method can also comprise an adding or multiplying of the first and the at least one further hit probability; in particular, in this way hit probabilities which are respectively assigned to the surface profile entries located in the database can be successively accumulated with each locating action. Furthermore, the method can comprise establishing that the total obtained reaches or exceeds a predetermined limit.

Upon reaching or exceeding the predetermined limit, a search for further surface profile entries in the database can be interrupted, for example. This embodiment is based on the idea that upon reaching or exceeding the limit, the remaining hit probability for possible further defect types is so small that these defect types can be disregarded, and it affords the advantage of a particularly fast method. In particular, the probability of the presence of particular types of defects can be estimated thereby if these defects have not yet been considered in the total; for example if, in a specific case, particularly defects of a type $T_1$ are of interest and if the total of hit probabilities belonging to the defect types $T_2$ to $T_n$ is already 92%, then it can be concluded that the probability of the presence of a hit of type $T_1$ is at most 8%.

The method can then further comprise an output of a defect message on an output device, the defect message preferably containing a display of the totalled hit probabilities and associated defect types. The defect message preferably contains information about the position of the workpiece in which the surface profile was detected.

This information can indicate to the user that, with a minimum probability provided by the limit, generally there is a defect on the workpiece and, if appropriate, it can indicate the position of the defect.

A method according to some embodiments of the disclosure herein may further comprise detecting at least one further surface profile, for example a plurality of further surface profiles, for which, if appropriate, analogously to the description above, at least one corresponding surface profile entry can be automatically found in each case which analogously provides an assignment to a defect type and to a hit probability for the further surface profile.

In this way, at least one planar region of the surface of the workpiece can be examined in different regions and optionally defects or types of defects in the region can be detected in a probabilistic manner.

According to some embodiments of a first method according to the disclosure herein, the at least one surface profile is detected and the surface profile entry is located during or after an automatic layer deposition of an automatic layer depositing process.

A second method according to the disclosure herein is used to create a database which is capable of analyzing defects in material ribbons laid on a fiber composite workpiece. The method comprises determining at least one surface profile resulting from a defect type. The determination procedure can be carried out by a user and/or can comprise a scanning of at least one surface profile of a defect of the defect type by a sensor device.

Furthermore, for each specific surface profile, the second method according to the disclosure herein comprises an automatic determination of a (hit) probability that a defect of the defect type is present during detection of the surface profile by a sensor device. The determination can take place on the basis of available data which, for example have been input by a user as empirical values and/or have been acquired by machine learning, and/or it can comprise the application of at least one statistical method. Data of this type may comprise probability values indicating that a defect of the defect type is really occurring.

Finally, the second method according to the disclosure herein comprises for each determined surface profile the storage of at least a first assignment of the determined surface profile to a defect type and to the hit probability as an entry of a database (or of a machine-managed data structure which forms the database on account of the at least one entry).

In particular, the second method according to the disclosure herein creates a database which is suitable for a use of the first method of the disclosure herein and thus creates a suitable basis for the mentioned advantages. The first and second methods according to the disclosure herein are supplemented thereby.

Thus, according to an embodiment of the first method of the disclosure herein, a database is used which is created according to a second method according to the disclosure herein. In particular, the first method according to the disclosure herein may include the steps of the second method according to the disclosure herein. However, it is understood that a database created according to the second method according to the disclosure herein can be present in a stored state and can be used for a plurality of examinations of all kinds of workpieces according to an embodiment of the first method of the disclosure herein.

According to some embodiments of the second method according to the disclosure herein, the entry stored in the database contains a characterization of the surface profile in the form of a sequence of step directions and step widths. A sequence of this type as the representative of the surface profile on one hand takes up little storage space and on the other hand, as described above, it can be re-located in the database later on using relatively few comparison steps, for example while using a first method of the disclosure herein.

Some embodiments of the second method according to the disclosure herein comprise generating at least one modified surface profile by modifying the determined at least one surface profile; the generation can be carried out automatically in particular, according to a pre-programmed algorithm. For each modified surface profile, the method further comprises determining a measured defect probability that the modified surface profile is detected by a sensor system based on a measured defect instead of on the determined surface profile. determining a (hit) probability that, upon detecting the modified surface profile, a defect of the defect type is present, and storing an assignment of the modified surface profile to the defect type and to the hit probability (for the modified surface profile) as an entry of the database.

The probability of a measured defect can be determined automatically based on available data, on machine learning and/or on at least one statistical method.

The hit probability for the modified surface profile can be determined based on the measured defect probability and on the hit probability for the associated (unmodified) surface profile, for example while considering possible matches of the modified surface profile with another surface profile which results from a defect of the same defect type, and possible matches with modified surface profiles of another surface profile which results from a defect of the same defect type.

A database created by an embodiment of this type and comprising assignments of this type considers possible inaccuracies of a sensor device while detecting a surface profile on a workpiece. Therefore, this embodiment allows a reliable detection of defects (particularly when used by an embodiment of the first method according to the disclosure herein) even if measurement errors of the sensor device are present.

A computer-readable storage medium according to the disclosure herein comprises instructions which are configured to effect the implementation of a first method according to the disclosure herein according to one of the embodiments described herein when a computer connected to an inspection device implements the instructions during an examination of a fiber composite workpiece.

The storage medium thus contains the program information which allows an automated implementation of the different embodiments of the first method according to the disclosure herein; the aforementioned advantages are provided thereby.

An inspection device according to the disclosure herein for checking fiber composite workpieces comprises at least one sensor device for scanning at least one surface of a workpiece and at least one computer unit which is configured to implement a first method according to the disclosure herein according to one of the embodiments mentioned herein for examining the fiber composite workpiece; in this case, the surface profile is recorded based on scanned values provided by the sensor device. The inspection device preferably allows the database to be amended (for example in a system-controlled manner and/or by a user).

An installation according to the disclosure herein for the automated production of fiber composite components comprises a laying head for automatically laying ribbons of material on a workpiece of a fiber composite component, a sensor device for detecting a surface profile of the workpiece and a control device for controlling the laying head and the sensor device. The sensor device has a camera and a laser light source arranged separately from the camera, the camera being attached to the laying head. The control device is configured to initiate, subject to a position of the camera on the workpiece, the projection by the laser light source of a light line onto a surface of the workpiece at a predetermined angle and the recording by the camera of the light line. The camera is configured to evaluate by a control at least one predetermined region of a recorded image, to create a height profile therefrom and to transmit the height profile to the control unit.

The installation according to the disclosure herein allows, by the sensor device, the detection of a surface profile and thereby provides an exemplary basis in terms of device for implementing a first method of the disclosure herein according to one of the embodiments described herein. In particular, the installation can comprise a computer unit which is configured to implement a first method of the disclosure herein according to one of the embodiments described herein for examining the workpiece, the detection of the surface profile being based on a scanning of at least one surface portion by the sensor device.

BRIEF DESCRIPTION OF THE DRAWINGS

In the following, features of some embodiments of the disclosure herein will be described in more detail with reference to drawings. It is understood that the individual schematic elements and components can also be combined and/or configured in ways other than those which have been shown and that the present disclosure is restricted the features which are shown.

In the schematic drawings.

DETAILED DESCRIPTION

Figure 1:
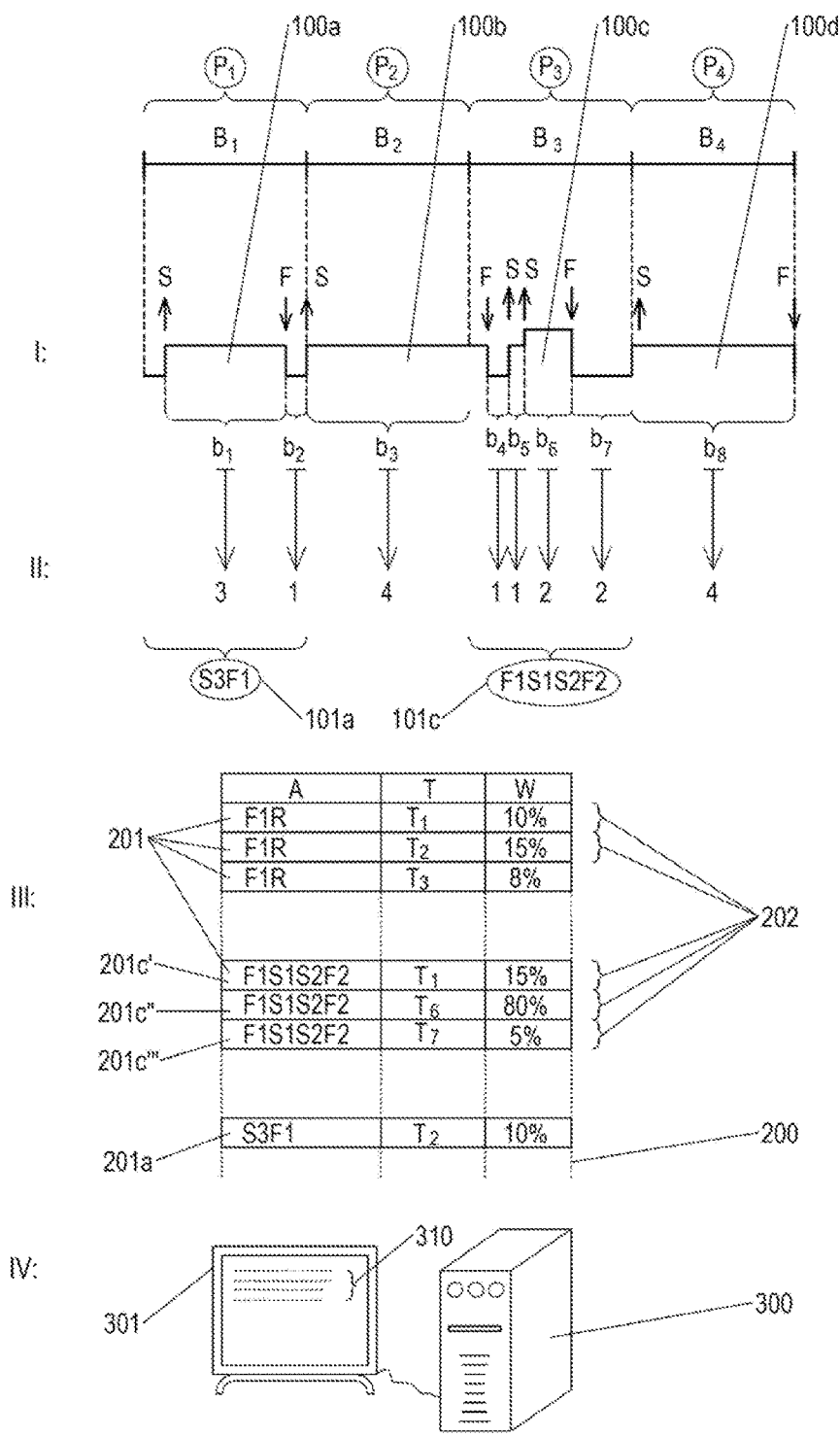
FIG. 1 shows a sequence of steps according to an embodiment of a first method of the disclosure herein.

In FIG. 1, various steps of a first method according to the disclosure herein are illustrated using a fictional example:

In step I, a plurality of surface structures 100a, 100b, 100c, 100d are detected which occur on a workpiece in different adjacently laid material ribbons in the positions $P_1$, $P_2$, $P_3$ and $P_4$; an intended ideal laying of the ribbons is schematically indicated by the adjacently arranged portions $B_1$, $B_2$, $B_3$, $B_4$, the width of which respectively corresponds to the width of the material ribbons.

In step II, the detected surface structures are characterized as a sequence of step directions and step widths; the respective step directions are characterized in the figure by corresponding arrows and by the letters "S" (for rising step) and "F" (for falling step).

As can be seen in the illustrated example, the surface profile 100a for example has a respective rising step and a falling step; in between is a step width $b_1$ and the falling step is followed by a step width $b_2$. The surface profiles 100b and 100d, on the other hand, do not contain any steps over the entire ribbon width $b_3$ and $b_8$. Finally, as characterized in the figure, surface profile 100c has a plurality of falling and rising steps having respective widths $b_4$, $b_5$, $b_6$ and $b_7$.

According to the characterization illustrated by way of example in FIG. 1, the established step widths $b_1, b_2, \ldots b_8$ are divided into a predetermined number of width categories. In this respect, the width categories are predetermined by suitable intervals. Thus, for example, a step width which is located in a (half open) interval of 0 mm to 1.5 mm could be assigned to a category 1, furthermore a step width in a (half open) interval of 1.5 mm to 3 mm could be assigned to a category 2, etc. For example, in the case of a ribbon width of 6 mm, according hereto four possible width categories would be established; it is understood that the classification is stated merely by way of example for explanation purposes and could also be selected differently; in particular, the intervals can also be of different lengths.

In the illustrated example, width $b_1$ is assigned to category 3, width $b_2$ is assigned to category 1, width $b_3$ is assigned to category 4 etc., as stated in FIG. 1. The widths $b_6$ and $b_7$ are both assigned to the same category 2 because, as can be seen in FIG. 1, although they are different in the illustrated example, they are located within a common interval on which the categorization is based.

The step-free surface structures 100b and 100d are obviously not based on any laying defect, which is why these surface structures need not be considered any further in the illustrated example.

The surface structures 100a and 100c are characterized by the sequences 101a and 101c in their corresponding step arrangements according to the established step directions and step widths, stated in FIG. 1 (the present example is based on a sequence from left to right); in particular the sequence "S3F1" is produced for surface profile 100a and the sequence "F1S1S2F2" is produced for surface profile 100c.

The positions $P_1$ and $P_3$ in which the surface profiles 100a and 100c were detected may be linked with the surface profiles 100a and 100c (or with the associated sequences) for example in a memory of a computer unit 300 which can be configured to implement the method. Thus, (after locating corresponding surface profile entries), the possible defect types and hit probabilities can be assigned to the corresponding positions in a display.

In step III, associated surface profile entries 201 are respectively sought in a database 200 for the surface profiles 100a, 100c characterized by the sequences 101a, 101c. In the illustrated case, this database is structured as a table which comprises a column A having different sequences which characterize a respective surface profile entry, a column T having possible defect types (for example "twist" or "overlap" or the like) and a column W having associated hit probabilities. The values for sequences shown in the figure, numbers of possible defect types and hit probabilities are purely fictional and merely serve to explain the method.

In the illustrated example, the different surface profile entries 201 in this database 200 provide via the lines 202, in which they are arranged in the table, a respective assignment of a possible sequence (and thereby of a possible surface profile) to a defect type and to a hit probability.

For example, for the surface profiles 100a, 100c and the associated sequences 101a, 101c which have been detected in step I, the database 200 comprises the surface profile entries 201a, 201c', 201c'', 201c'''; in particular, it is considered in table 200 that the surface profile 100c, characterized by sequence 100c can be based on different defect types. The lines in which the surface profile entries are arranged in the table, provide for example the possible defect types $T_1$, $T_6$ and $T_7$ for the surface profile 100c as well as the associated hit probabilities that surface profile 100c, when it is detected is actually based on a defect of the respective type; the same applies analogously to surface profile 100a.

According to some embodiments of the first method, in the provided example at least one of the (present) three surface profile entries 201c', 201c'' and 201c''' is found. A variant may be possible, according to which a plurality of, or even all respectively matching surface profile entries are found.

In this case, the associated hit probabilities can be added successively. On reaching an (intermediate) total which attains or exceeds a predetermined limit, the search for further surface profile entries which match (in this example, surface profile 100c) can be interrupted and thus the duration of the method can be shortened.

In the illustrated example, for example the search to locate the surface profile entries 201c' and 201c'' could be ended, because the totalled hit probabilities thereof at a level of 95% exceed a limit of, for example 90% and other remaining possibilities of defect types, on which the surface profile 100c could be based, together only have a probability of 5% and can thus be disregarded.

In step IV, information about the surface profiles 101a, 101c is displayed on a display device 301 using the assignments in the located surface profile entries. A display 310 of this type could, for example contain the information that a defect of type $T_1$ is present in position $P_3$ with a hit probability of 15% and a defect of type $T_6$ is present with a hit probability of 80%, that a defect of one of the types $T_1$ or $T_6$ is present in position $P_3$ with a hit probability of 95% and/or that the probability that a defect of type $T_2$ is present in position $P_3$ is at most 5%.

This information can make it easier for a user to take suitable measures.

Figure 2:
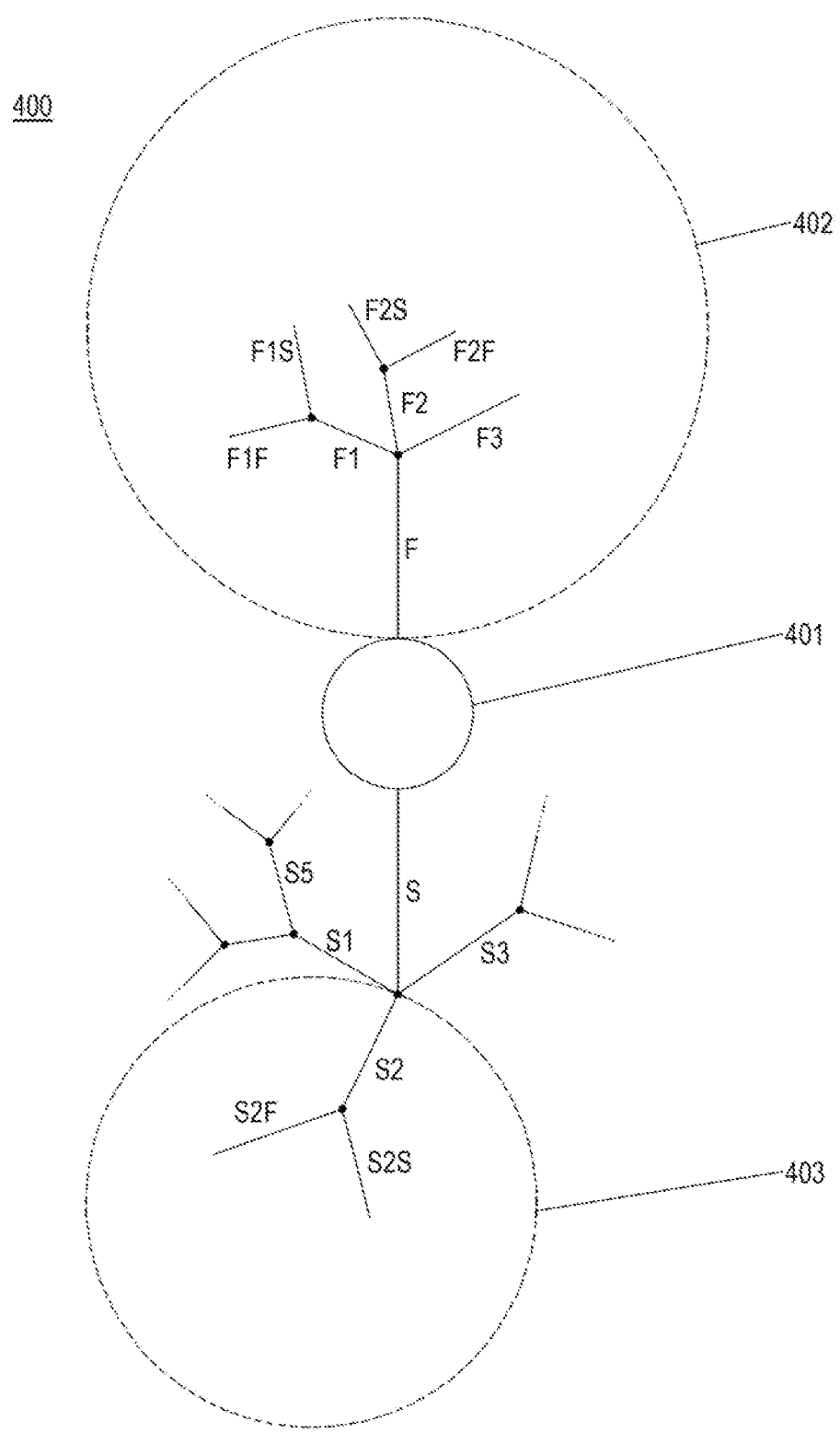
FIG. 2 shows an exemplary search tree suitable for locating a surface structure entry in a database.

FIG. 2 shows by way of example a suitable construction of a search tree 400 by which the database may be structured; in this figure as well, the entered values are purely fictional.

For example, if a surface profile produces a sequence S2F3, then a database management system can firstly successively rule out from further examination all sequences beginning with F from the subtree 402 starting with the root 401, it can then restrict the further search on the subtree 403 to sequences in which an "S" is followed by a 2, etc. It is understood that a search tree can also be of a different structure than the one shown. The nodes preferably correspond to one or more surface profile entries or are linked thereto, so that the possible defect types and associated hit probabilities can be detected using the nodes.

Figure 3:
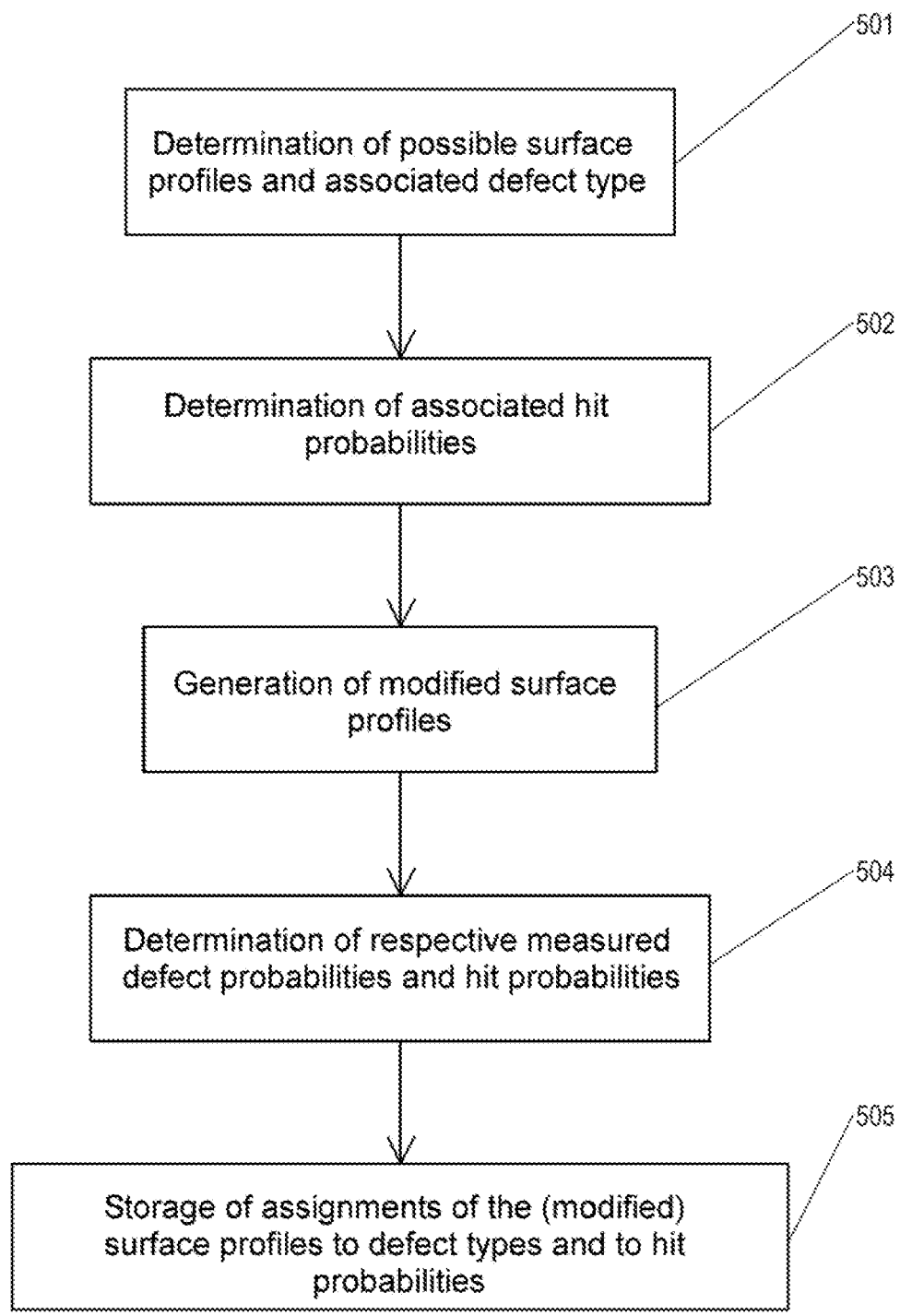
FIG. 3 shows a sequence of steps according to a second method of the disclosure herein.

FIG. 3 schematically shows a sequence of method steps for creating a database according to an exemplary embodiment of the second method according to the disclosure herein.

The method comprises a step 501 in which possible surface profiles are determined which can result from a defect of a specific defect type. As mentioned, the determination and assignment to the respective defect type can be performed by a user and/or can comprise a scanning of a defect of a known defect type by a sensor device, and a recording of detected surface profiles.

The method also comprises a step 502 in which hit probabilities are respectively determined for the determined surface profiles, i.e. values which are respectively assigned to the probabilities that during the detection of the surface profile by a sensor device, a defect of the defect type is present; this determination can be made on the basis of known data (for example from empirical values), on the basis of at least one statistical method and/or on the basis of machine learning.

In a step 503, modified surface profiles are generated from at least one of the possible determined surface profiles.

In a step 504, for each modified surface profile generated thus, one measured defect probability is determined (i.e. a value which is assigned to the probabilities that the modified surface profile is detected by a sensor device based on a measured defect instead of on the determined surface profile) as well as a hit probability (a value which is assigned to the probabilities that a detection of the modified surface profile respectively indicates the defect type).

Finally, in a step 505, assignments of the determined and of the modified surface profiles respectively to defect types and associated hit probabilities are stored in a data structure which may be managed by a suitable database management system and which produces the database.

The subject matter disclosed herein can be implemented in or with software in combination with hardware and/or firmware. For example, the subject matter described herein can be implemented in software executed by a processor or processing unit. In one exemplary implementation, the subject matter described herein can be implemented using a computer readable medium having stored thereon computer executable instructions that when executed by a processor of a computer control the computer to perform steps. Exemplary computer readable mediums suitable for implementing the subject matter described herein include non-transitory devices, such as disk memory devices, chip memory devices, programmable logic devices, and application specific integrated circuits. In addition, a computer readable medium that implements the subject matter described herein can be located on a single device or computing platform or can be distributed across multiple devices or computing platforms.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

What is claimed is:

1. A method for probabilistic detection of defects in ribbons of material which have been laid on a fiber composite workpiece, the method comprising:
    using an inspection device in electronic communication with a database and comprising at least one sensor device to examine the fiber composite workpiece;
    detecting at least one surface profile of a workpiece having laid material ribbons using the inspection device;
    locating a surface profile entry in the database, wherein the surface profile entry provides an assignment of the at least one surface profile that was detected to a defect type and to a hit probability that the at least one surface profile that was detected is based on a defect of the defect type; and
    displaying an output comprising at least one defect type being assigned to the surface profile entry and the hit probability on an output device;
    wherein the surface profile entry is a first surface profile entry, the defect type is a first defect type and the hit probability is a first hit probability, and wherein the method comprises locating at least one further surface profile entry in the database, the at least one further surface profile entry providing an assignment of the surface profile entry to at least one further defect type which is different from the first defect type and provides at least one further hit probability that the at least one surface profile that was detected is based on a defect of the at least one further defect type;
    totaling the first hit probability and the at least one further hit probability to create a totaled hit probability;
    establishing that the totaled hit probability reaches or exceeds a predetermined limit; and
    outputting the totaled hit probability and associated defect types.

2. The method of claim 1, wherein detecting the at least one surface profile comprises scanning at least one surface portion of the workpiece by the at least one sensor device.

3. The method of claim 1 which comprises a characterization of the at least one surface profile, that was detected, by a sequence, the sequence comprising information about step directions, step widths and/or step heights which occur in the surface profile, and the surface profile entry being located on a basis of the sequence.

4. The method of claim 3, wherein the characterization comprises a categorization of step widths into a predetermined number of width categories.

5. The method of claim 3, wherein the locating procedure is carried out by a successive comparison of individual step directions and/or step widths and/or step heights, described by the sequence, using nodes of a search tree.

6. The method of claim 5, wherein the search tree comprises a neural network.

7. The method of claim 1, wherein the hit probability includes:
    a surface profile probability that the surface profile is detected when a defect of the defect type occurs;
    a measured defect probability that the at least one surface profile that was detected is based on at least one measured defect; and/or
    an occurrence probability indicating that a defect of the defect type is occurring on the fiber composite workpiece.

8. The method of claim 1 further comprising displaying information indicating a position of the fiber composite workpiece in which the surface profile was detected.

9. The method of claim 1, the output further comprising a determination that the hit probability reaches or exceeds a predetermined minimum value.

10. A non-transitory computer-readable storage medium having instructions which are configured to effect an implementation of a method according to claim 1 when a computer, connected to the inspection device, implements the instructions during an examination of a fiber composite workpiece.

11. An inspection device for checking fiber composite workpieces, the inspection device comprising:
    at least one sensor device configured for scanning at least one surface profile of a workpiece; and
    at least one computer unit which is in electronic communication with a database and configured to implement a method for probabilistic detection of defects in ribbons of material which have been laid on a fiber composite workpiece, the method comprising:
        detecting at least one surface profile of a workpiece having laid material ribbons;
        locating a surface profile entry in the database, wherein the surface profile entry provides an assignment of the at least one surface profile that was detected to a defect type and to a hit probability that the at least one surface profile that was detected is based on a defect of the defect type;
    the method being performed for examining the fiber composite workpiece; and
        displaying an output comprising at least one defect type being assigned to the surface profile entry and the hit probability on an output device;
        wherein the surface profile entry is a first surface profile entry, the defect type is a first defect type and the hit probability is a first hit probability, and wherein the method comprises locating at least one further surface profile entry in the database, the at least one further surface profile entry providing an assignment of the surface profile entry to at least one further defect type which is different from the first and provides at least one further hit probability that the at least one surface profile that was detected is based on a defect of the at least one further defect type;
        totaling the first hit probability and the at least one further hit probability to create a totaled hit probability;
        establishing that the totaled hit probability reaches or exceeds a predetermined limit; and
        outputting the totaled hit probability and associated defect types.

* * * * *